US008900852B2

(12) United States Patent
Nakatani et al.

(10) Patent No.: US 8,900,852 B2
(45) Date of Patent: Dec. 2, 2014

(54) AMPLIFICATION REACTION VESSEL, AND METHOD OF MANUFACTURING THE SAME

(75) Inventors: Masaya Nakatani, Takarazuka (JP); Tetsuo Yukimasa, Nara (JP)

(73) Assignee: Panasonic Corporation, Osaka (JP)

(*) Notice: Subject to any disclaimer, the term of this patent is extended or adjusted under 35 U.S.C. 154(b) by 2260 days.

(21) Appl. No.: 10/984,500

(22) Filed: Nov. 9, 2004

(65) Prior Publication Data

US 2006/0160097 A1 Jul. 20, 2006

(30) Foreign Application Priority Data

Nov. 17, 2003 (JP) ................................ 2003-386614

(51) Int. Cl.

*C12M 1/34* (2006.01)
*C12M 1/40* (2006.01)
*B01L 3/00* (2006.01)
*B01L 7/00* (2006.01)

(52) U.S. Cl.

CPC ....... *B01L 3/50851* (2013.01); *B01L 3/502707* (2013.01); *B01L 3/502715* (2013.01); *B01L 7/52* (2013.01); *B01L 2300/0816* (2013.01); *B01L 2300/0822* (2013.01); *B01L 2400/0406* (2013.01); *B01L 2400/086* (2013.01)

USPC .................. 435/287.2; 435/288.3; 435/299.1; 435/303.1; 435/305.4; 422/551; 422/559

(58) Field of Classification Search

CPC ...... C12M 23/16; C12M 27/20; C12M 41/24; B01L 3/502746; B01L 3/502753; B01L 7/52; B01L 2400/086

See application file for complete search history.

(56) References Cited

U.S. PATENT DOCUMENTS 4,683,202 A 7/1987 Mullis
4,891,120 A * 1/1990 Sethi et al. .................... 204/600
4,963,498 A * 10/1990 Hillman et al. ................ 436/69
5,707,799 A * 1/1998 Hansmann et al. ............... 435/6
6,096,656 A * 8/2000 Matzke et al. ................ 438/702
6,368,871 B1 * 4/2002 Christel et al. ................ 436/180
6,457,854 B1 * 10/2002 Koop et al. ................... 366/336
6,663,697 B1 * 12/2003 Kottenstette et al. ........... 96/101
6,699,392 B1 * 3/2004 Manginell et al. ............ 210/656
6,929,750 B2 8/2005 Laurell et al.
8,304,230 B2 * 11/2012 Toner et al. ................ 435/288.5
2002/0081741 A1 * 6/2002 Braun et al. .................... 436/43

FOREIGN PATENT DOCUMENTS

JP 62-281 1/1987
JP 2002-207031 7/2002

OTHER PUBLICATIONS

R.P. Oda et al., "Infrared-Mediated Thermocycling for Ultrafast Polymerase Chain Reaction Amplification of DNA", Analytical Chemistry, vol. 70, No. 20, pp. 4361-4368, Oct. 15, 1998.

* cited by examiner

*Primary Examiner* — William H Beisner
(74) *Attorney, Agent, or Firm* — RatnerPrestia

(57) ABSTRACT

A nucleic acid amplification reaction vessel has a substrate, a cavity formed in the substrate, a cover plate for sealing the cavity, and a sample-injection inlet formed in the cover plate. The cavity includes a columnar structure connected to the cover plate or the substrate. The nucleic acid amplification reaction vessel allows fast temperature increase or decrease of sample liquid.

10 Claims, 7 Drawing Sheets

AMPLIFICATION REACTION VESSEL, AND METHOD OF MANUFACTURING THE SAME

BACKGROUND OF THE INVENTION

1. Field of the Invention

The present invention relates to a nucleic acid amplification reaction vessel used for amplifying nucleic acid using polymerase chain reaction, and a method of manufacturing the nucleic acid amplification reaction vessel.

2. Background Art

Recently, technology related to genetic information has been actively developed. Especially in a medical field, genes related to diseases have been analyzed to allow curing of the diseases at molecule level. Genetic diagnosis allows a tailor-made medical care corresponding to an individual patient. In a drug manufacturing field, genetic information is used to identify protein molecules of antibody or hormone, and the protein molecules are used as chemicals.

In agricultural and food fields, also, products using much genetic information are manufactured.

One of the most important methods is amplification reaction of nucleic acid in the technology related to genetic information. A polymerase chain reaction method is technology of largely amplifying only a specific part of a gene, and is employed in a broad range such as study of molecular biology or the like, medical microbiology, clinical diagnosis of genetic disorders, and legal medicine. In genetic diagnosis technology especially in a clinical field, further speedy analysis is desired, and high throughput technology is desired to be developed in the polymerase chain reaction method.

The polymerase chain reaction method has the following processes:

(1) a thermal deforming process of dissociating double-strand DNA (deoxyribonucleic acid) to single-strand DNA;

(2) an annealing process of binding primers; and (3) an elongation reaction process of elongating DNA with polymerase.

The three processes are generally defined as one cycle, and these processes are performed by 30 to 35 cycles. Japanese Patent Unexamined Publication No. S62-000281 discloses the following treatment conditions: (1) a thermal deforming process is performed at 94° C. for one minute; (2) an annealing process is performed at 50° C. to 60° C. for one minute; and (3) an elongation reaction process is performed at 72° C. for 1 to 5 minutes.

Japanese Patent Unexamined Publication No. 2002-207031 discloses a vessel or a chip used for the polymerase chain reaction. For example, a groove for holding a capillary is formed in an upper substrate, and the capillary is disposed and bonded between the upper substrate and a lower substrate. Thus, a sample containing nucleic acid to be amplified can be inserted into the capillary, and the temperature of the capillary is controlled to amplify the nucleic acid in the sample.

A device for speeding up the polymerase chain reaction is also developed. LightCycler manufactured by Loche uses hot air as a heat source, and the sample is supplied to a vessel formed of a glass capillary, for speeding up. SmartCycler® manufactured by Cepheid uses a dedicated polypropylene-made tube having a thin tube wall to speed up the polymerase chain reaction.

However, the polymerase chain reaction requires 30 or more repetitions of temperature variation by about 40° C. In a conventional device used for the polymerase chain reaction, the sample is supplied to a polypropylene-made tube and simultaneously an aluminum block is used to increase temperature, so that treatment time not less than several hours is required for completing the polymerase chain reaction.

In the method disclosed by Japanese Patent Unexamined Publication No. 2002-207031, the capillary is trapped in the upper and lower substrates, so that some increase of thermal conductivity can be expected. However, the capillary, the upper substrate, and the lower substrate are individually formed, and then bonded using an adhering technology. In this case, a heat barrier made of adhesive material or the like can be formed between the upper or lower substrate and the capillary to decrease the thermal conductivity, and fast increase or decrease of the temperature can be disadvantageously disturbed.

A device using hot air as the heat source allows speeding up, but even then treatment time not less than tens of minutes is required.

Any of conventional technologies uses a dedicated vessel such as a capillary to aim to speeding up. Therefore, a pre-treatment for the polymerase chain reaction, for example extraction of DNA from blood, must be performed in a batch method, so that handling of the sample becomes complicated.

SUMMARY OF THE INVENTION

A nucleic acid amplification reaction vessel of the present invention has the following elements:

a substrate;

a cavity formed in the substrate;

a cover plate for sealing the cavity; and a sample-injection inlet formed in the cover plate.

The inside of the cavity is provided with a columnar structure connected to the cover plate or the substrate. When heating or cooling is performed from one or both of the cover plate and the substrate constituting the nucleic acid amplification reaction vessel, the columnar structure promotes heat transfer and the temperature of solution containing the nucleic acid in the cavity can be varied fast. As a result, the nucleic acid amplification reaction vessel certainly allows fast polymerase chain reaction.

In the nucleic acid amplification reaction vessel of the present invention, the cavity has a meander shape or a spiral shape. Using one of these shapes as the cavity shape increases the surface area of the cavity with respect to the volume of the cavity, so that efficient heat exchange between the cavity and the substrate is allowed.

In a manufacturing method of the nucleic acid amplification reaction vessel of the present invention, the reaction vessel has a columnar structure integrated with the cover plate or the substrate in the cavity. In the manufacturing method, the cover plate and the substrate are bonded together by one of an anode bonding method and a direct bonding method. Thus, the manufacturing method can realize a nucleic acid amplification reaction vessel having the following characteristics:

no other material is used on the bonding surface between the cover plate and the substrate except for themselves;

the thermal conductivity is high; and an excess component does not dissolve into the nucleic acid amplification reaction vessel.

In the manufacturing method of the nucleic acid amplification reaction vessel of the present invention, the reaction vessel has a cavity having a meander shape or a spiral shape. By bonding the cover plate and the substrate together by one of an anode bonding method and a direct bonding method, the bonding surface between the cover plate and the substrate has only material of them.

A nucleic acid amplification reaction vessel and a manufacturing method thereof of the present invention realize a structure allowing fast heating or cooling, thereby accurately and fast amplifying the DNA in a sample. A chip type nucleic acid amplification reaction vessel that facilitates handling of a sample and is used for nucleic acid amplification reaction, and a manufacturing method thereof can be provided.

DETAILED DESCRIPTION OF THE INVENTION

Figure 1:
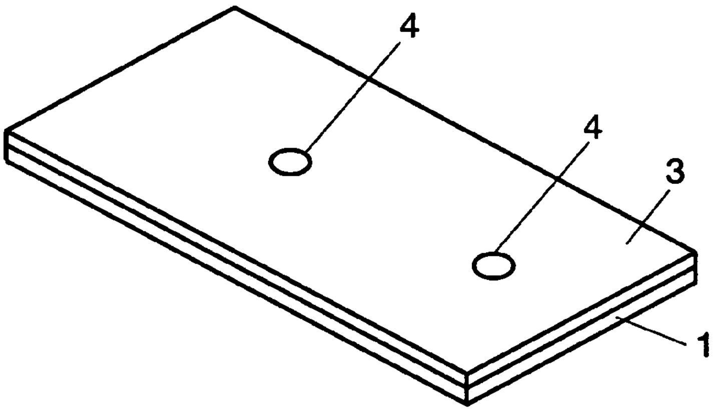
FIG. 1 is a perspective view showing the structure of a nucleic acid amplification reaction vessel in accordance with exemplary embodiment 1 of the present invention.

A nucleic acid amplification reaction vessel of the present invention is used for amplifying nucleic acid. The vessel has the following elements:

- a substrate;
- a cavity formed in the substrate;
- a cover plate for sealing the cavity; and
- a sample-injection inlet formed in the cover plate.

The inside of the cavity is provided with a columnar structure connected to the cover plate or the substrate. When heating or cooling is performed from the cover plate, the substrate, or both of them in the nucleic acid amplification reaction vessel used in a nucleic acid amplifying method in which polymerase chain reaction is employed, heat is fast transferred to the columnar structure. Therefore, the temperature of solution containing nucleic acid in the cavity can be fast varied, and fast polymerase chain reaction can be certainly performed.

In the nucleic acid amplification reaction vessel of the present invention, the cross section of the columnar structure has a circular shape, an elliptic shape, or a bent shape. Selecting these shapes allows efficient heat exchange, and hence fast polymerase chain reaction can be performed.

The nucleic acid amplification reaction vessel of the present invention may have a plurality of columnar structures. The plurality of columnar structures allow more efficient heat exchange.

The nucleic acid amplification reaction vessel of the present invention is an integral structure reaction vessel where the columnar structure is made of the same material as that of the cover plate or the substrate and the bonding surface does not exist. The use of the same material and the non-existence of the bonding surface remove a barrier against heat exchange, so that faster polymerase chain reaction can be performed.

In the nucleic acid amplification reaction vessel of the present invention, the substrate and the columnar structure are directly bonded together. Fast polymerase chain reaction having high productivity is therefore allowed.

In the nucleic acid amplification reaction vessel of the present invention, the cover plate and the columnar structure are directly bonded together. Fast polymerase chain reaction having high productivity is therefore allowed.

In the nucleic acid amplification reaction vessel of the present invention, the cavity has a meander shape or a spiral shape. In the cavity having this shape, it should be said that the wall itself of a meander-shaped or spiral groove functions as a columnar structure. Employing the meander shape or spiral shape as the cavity shape increases the surface area of the cavity with respect to the volume of the cavity, so that efficient heat exchange between the cavity and the substrate is allowed.

In the nucleic acid amplification reaction vessel of the present invention, the cover plate is made of glass and the substrate is made of silicon. Since the substrate is made of silicon, the reaction vessel can obtain high thermal conductivity. Since the cover plate is made of glass, the reaction vessel can be manufactured by a bonding method of the cover plate and the substrate made of silicon: by an anode bonding method or by a direct bonding method, for example. As a result, the thermal conductivity between the substrate and the cover plate is improved, and an excess component does not dissolve into the nucleic acid amplification reaction vessel during polymerase chain reaction.

In a manufacturing method of the nucleic acid amplification reaction vessel of the present invention, the bonding between the cover plate and the substrate is performed by one of the anode bonding method and the direct bonding method when the reaction vessel having a columnar structure integrated with the cover plate and the substrate in the cavity is manufactured. In the bonding method, the bonding surface between the cover plate and the substrate includes only materials of them, and no other material is used. A nucleic acid amplification reaction vessel has high thermal conductivity, and the excess component does not dissolve into the nucleic acid amplification reaction vessel.

In a manufacturing method of the nucleic acid amplification reaction vessel of the present invention, the bonding between the cover plate and the substrate is performed by one of the anode bonding method and the direct bonding method when the reaction vessel having a meander-shaped or spiral cavity is manufactured. In the bonding method, the bonding surface between the cover plate and the substrate includes only materials of them.

Exemplary Embodiment 1

A nucleic acid amplification reaction vessel in accordance with exemplary embodiment 1 of the present invention will be described in detail.

Figure 2:
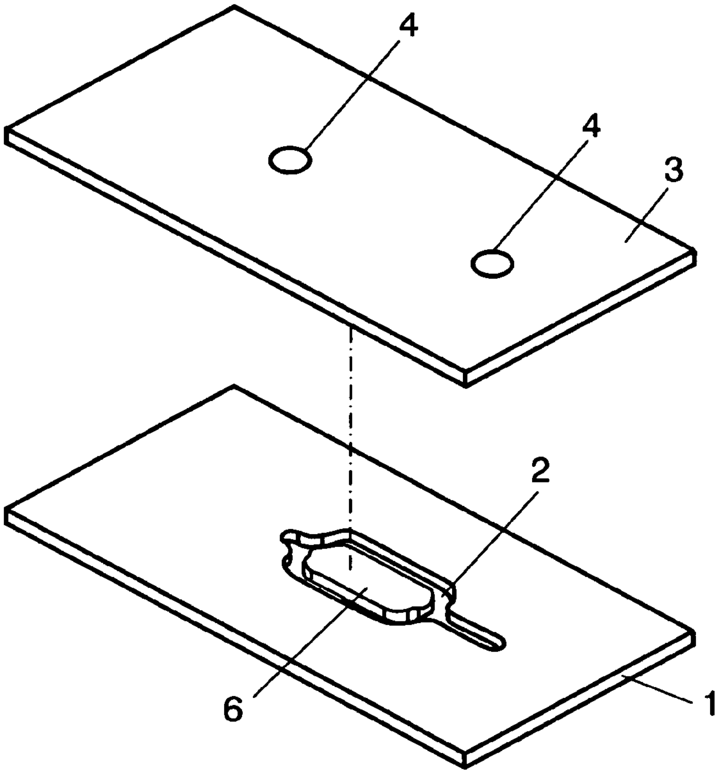
FIG. 2 is an exploded perspective view of the nucleic acid amplification reaction vessel in accordance with exemplary embodiment 1.

FIG. 1 and FIG. 2 are views showing a structure of a nucleic acid amplification reaction vessel in accordance with exemplary embodiment 1 of the present invention.

The nucleic acid amplification reaction vessel in accordance with exemplary embodiment 1 has cavity 2 for retaining sample liquid in substrate 1 made of silicon. Elliptic columnar structure 6 made of silicon is disposed in cavity 2.

Cover plate 3 made of glass or the like is bonded with the upper surfaces of substrate 1 and elliptic columnar structure 6, and cavity 2 is blocked from the outside. A sample can be contained in cavity 2 through sample-injection inlets 4 formed in cover plate 3. Here, an adhesive or the like is not used for bonding substrate 1 and cover plate 3 together, and substrate 1 made of silicon and cover plate 3 made of glass are bonded together by intermolecular bonding.

Materials that do not react to the sample liquid are adequate as those of substrate 1 and cover plate 3. In addition to silicon and glass, for example, semiconductor such as germanium or the like, quartz, ceramics, and a single crystal substrate of lithium titanate or lithium niobate can be employed. When these materials are employed, a bonding technology described in exemplary embodiment 2 can be used. For example, the direct bonding or the anode bonding method, namely intermolecular bonding, can be used. These bonding technologies allow efficient manufacturing of the nucleic acid amplification reaction vessel of the present invention.

In the nucleic acid amplification reaction vessel of the present invention, elliptic columnar structure 6 and substrate 1 are formed as one structure using the same material, so that the barrier against thermal conductivity can be reduced.

Cover plate 3 and substrate 1 are directly bonded together by intermolecular bonding, and different kind of material such as an adhesive is not used. Thermal barrier against thermal conductivity exists little to allow fast thermal conduction.

Figure 3:
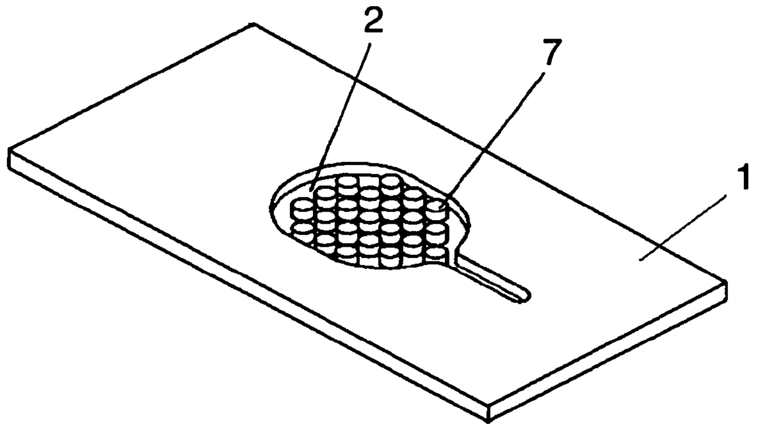
FIG. 3 is a perspective view of an essential part of the structure of another nucleic acid amplification reaction vessel in accordance with exemplary embodiment 1.
Figure 4:
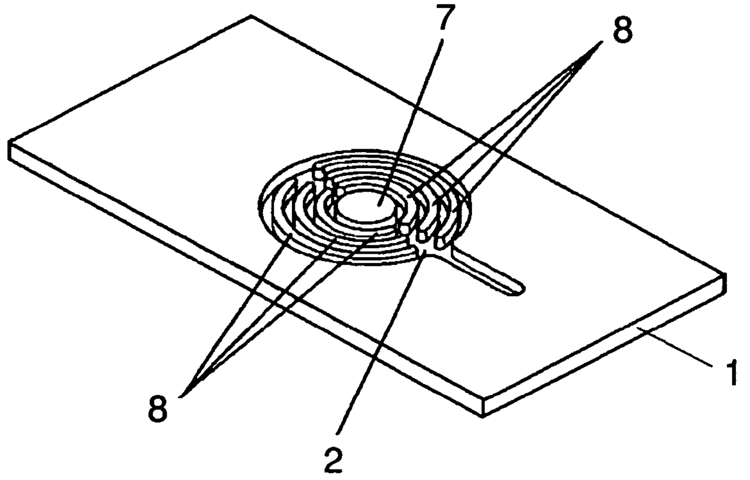
FIG. 4 is a perspective view of an essential part of the structure of still another nucleic acid amplification reaction vessel in accordance with exemplary embodiment 1.

Columnar structure 6 may have not only the elliptic shape shown in FIG. 2 but also a circular shape or a bent shape. When the number of columnar structures 6 is two or more, an effect of promoting thermal conduction further increases. For example, a plurality of circular columnar structures 7 or bent-shaped columnar structures 8 can be formed as shown in FIG. 3 or FIG. 4. When columnar structures 6, 7 and 8 are formed, various capacities, volumes, and wall surface areas of cavities 2 are obtained. Especially, when these factors affect the nucleic acid amplification reaction, the capacity and volume, the wall surface area, and the number of columnar structure 6, 7 or 8, in addition to a temperature increase/decrease characteristic, are optimized, thereby obtaining a predetermined performance.

Columnar structure 6, 7 or 8 and substrate 1 or cover plate 3 are formed as one structure in embodiment 1; however, columnar structure 6, 7 or 8 and substrate 1 or cover plate 3 may be formed individually and then integrated using the direct bonding technology. Even in the latter manufacturing method, a nucleic acid amplification reaction vessel having thermal conductivity substantially the same as that of the reaction vessel of embodiment 1 can be realized.

Exemplary Embodiment 2

A nucleic acid amplification reaction vessel in accordance with exemplary embodiment 2 of the present invention will be described.

Figure 5:
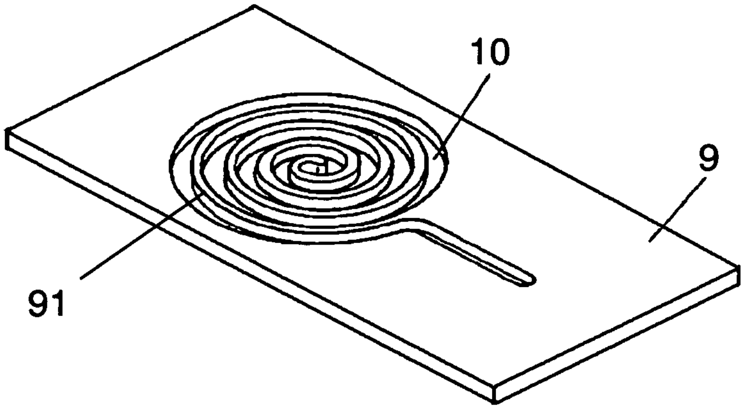
FIG. 5 is a perspective view of an essential part of the structure of a nucleic acid amplification reaction vessel in accordance with exemplary embodiment 2 of the present invention.

FIG. 5 is a perspective view of substrate 9 of the nucleic acid amplification reaction vessel in accordance with exemplary embodiment 2. Spiral cavity 10 is formed in substrate 9 made of silicon, and the barrier of cavity 10 is integrated with silicon substrate 9. In other words, cavity 10 is surrounded by substrate 9 or columnar structure 91. The spiral shape of cavity 10 allows cavity 10 to be formed in a narrow region in substrate 9 in a concentrated manner. Fast heat exchange between sample liquid and substrate 9 is therefore performed, and a reaction vessel having high soaking property can be advantageously designed.

Figure 6:
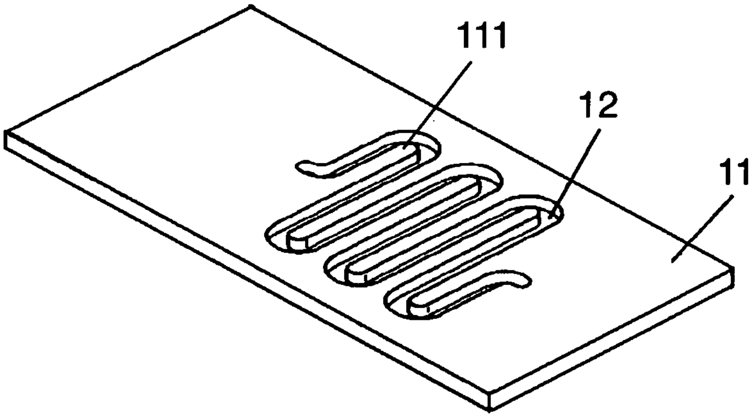
FIG. 6 is a perspective view of an essential part of the structure of another nucleic acid amplification reaction vessel in accordance with exemplary embodiment 2.

FIG. 6 shows another example where meander-shaped cavity 12 is formed in substrate 11 made of silicon. In other words, cavity 12 is surrounded by substrate 11 or columnar structure 111. Advantage of the meander shape of cavity 12 is the same as that of the spiral shape discussed above. Additionally, in the case of the meander shape, sample liquid flows in one direction on substrate 11, so that a sample-injection inlet (not shown) can be formed at an end of substrate 11. In the case of the spiral shape, one end of the sample-injection inlet is positioned at the center of the spiral. Whether the cavity is formed in a spiral shape or in a meander shape can be determined in response to a sample or a processing protocol.

Next, a manufacturing method of the nucleic acid amplification reaction vessel is described with reference to FIG. 7 to FIG. 12.

An example is described where a nucleic acid amplification reaction vessel for polymerase chain reaction is manufactured using a silicon single crystal plate with 500 μm of thickness as substrate 13.

Figure 7:
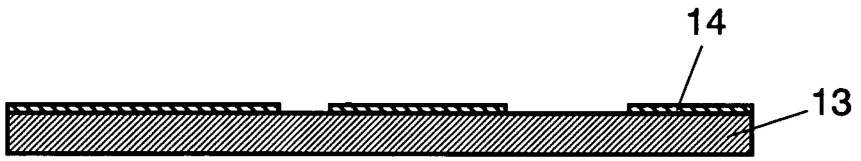
FIG. 7 to FIG. 12 are sectional views of a manufacturing process of the nucleic acid amplification reaction vessel in accordance with exemplary embodiment 2.
Figure 8:
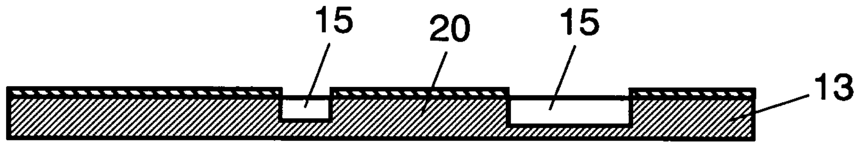

Firstly, mirror polished substrate 13 made of 500 μm thick silicon and cover plate 16 made of 400 μm thick glass are prepared. Resist mask 14 is formed in a predetermined pattern as shown in FIG. 7 on substrate 13 made of silicon, and cavity 15 is formed by dry etching using $SF_6$ as shown in FIG. 8. The depth of the etching depends on required sample volume, but it is appropriate that the depth is about 150 to 400 μm. Forming cavity 15 leads to forming of columnar structure 20.

For forming cavity 15 in substrate 13 made of silicon, a dry etching method such as a reactive ion etching (RIE) and a wet etching method using strong alkaline etching liquid or the like can be used when substrate 13 is a semiconductor made of silicon. When substrate 13 is made of glass, a wet etching method using hydrofluoric acid can be used.

Especially, it is preferable that the semiconductor made of silicon or the like is used as substrate 13. That is because using micromachining technology well-known in a semiconductor field allows micro cavity 15 and columnar structure 20 arranged at high density to be precisely machined or processed.

Figure 9:
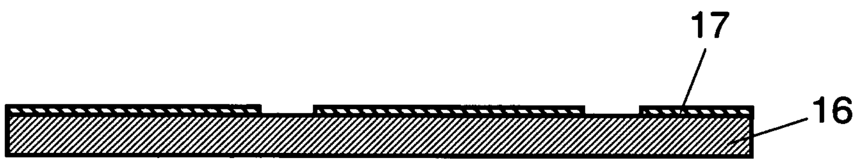
Figure 10:
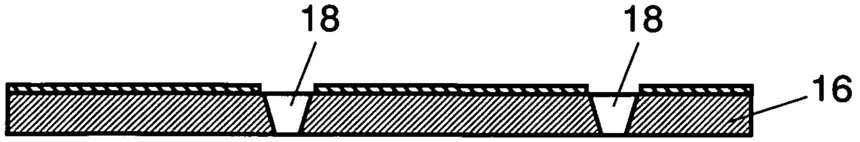

Next, resist mask 17 is formed in a glass substrate defining cover plate 16 as shown in FIG. 9, and sample-injection inlets 18 are then formed by a sandblast method to provide cover plate 16 as shown in FIG. 10. At this time, for forming sample-injection inlets 18, in addition to the sandblast method, a wet etching method using hydrofluoric acid or a dry etching method using $SF_6$ gas, $CF_4$ gas, $C_3F_8$ gas, or $C_4F_8$ gas can be employed.

In selecting a forming method of sample-injection inlets 18, an optimal method can be selected in response to a processing precision required for sample-injection inlets 18.

Figure 11:
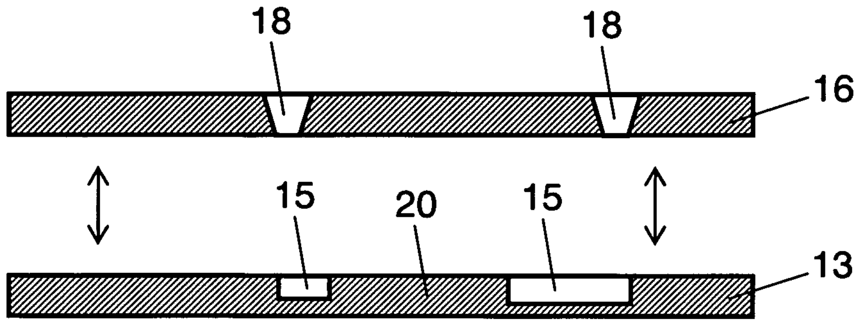
Figure 12:
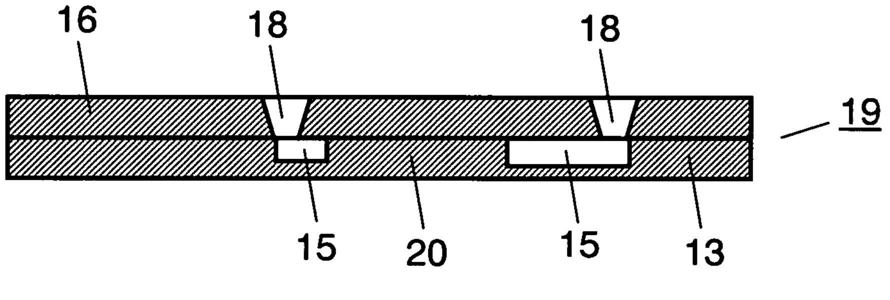

Next, as shown in FIG. 11, the surfaces of substrate 13 made of silicon and cover plate 16 made of glass are cleaned with an acid cleaning agent, and substrate 13 and cover plate 16 are then adhered to each other so as to prevent air from coming into a gap between them. Substrate 13 and cover plate 16 are bonded by direct bonding without using an adhesive by heating them at 300° C. for three hours in the adhered state, and nucleic acid amplification reaction vessel 19 shown in FIG. 12 is provided. After that, if necessary, the vessel is cut to form a chip-like vessel, and a small nucleic acid amplification reaction vessel is obtained.

Thanks to the direct bonding technology, substrate 13 made of silicon and cover plate 16 made of glass are firmly bonded by intermolecular bonding, and any excess component such as an adhesive therefore does not exist in a place with which solution can contact. Therefore, the excess component does not dissolve into the vessel during the polymerase chain reaction.

The substrate and cover plate are heated during the adhesion at 300° C. for three hours in the direct bonding method in embodiment 2; however, heating temperature may be changed depending on glass material. About 250° C. is enough to directly bond glass material containing sodium or potassium, but about 400° C. is required to directly bond glass material containing neither sodium nor potassium. The glass material may be a material such as quartz glass containing no impurity. In this case, the bonding temperature must be increased to 500° C. or higher. The material of cover plate 16 may be silicon. In this case, also, substrate 13 made of silicon including cavity 15 and cover plate 16 made of silicon including sample-injection inlets 18 can be bonded together by direct bonding. Temperature for the direct bonding at this time must be 500° C. or higher.

As a bonding method allowing intermolecular bonding other than the method discussed above, the following method may be employed:

an anode bonding method of heating substrate 13 and cover plate 16 while applying voltage to them; or a normal-temperature direct bonding method of irradiating substrate 13 and cover plate 16 with plasma in vacuum and bonding them together.

Next, a procedure of amplifying nucleic acid with the nucleic acid amplification reaction vessels discussed in embodiment 1 and embodiment 2 is described hereinafter.

A means for increasing or decreasing temperature of the nucleic acid amplification reaction vessels of the present invention is not especially limited. A conventional method using an aluminum block may be employed. Otherwise, as discussed in the conventional technology section, the following method may be employed:

a method such as LightCycler using hot air as a heat source;

a method using a tungsten lamp as an infrared radiation source (R. P. Oda et al., Infrared-Mediated Thermocycling for Ultrafast Polymerase Chain Reaction Amplification of DNA, Analytical Chemistry, 1998, 70, 4361-4368); or a method using electromagnetic induction heating.

Shapes of cavities of the vessels used for nucleic acid amplification reaction are shown in FIG. 13A to FIG. 13D.

Comparative Example

Figure 13A:
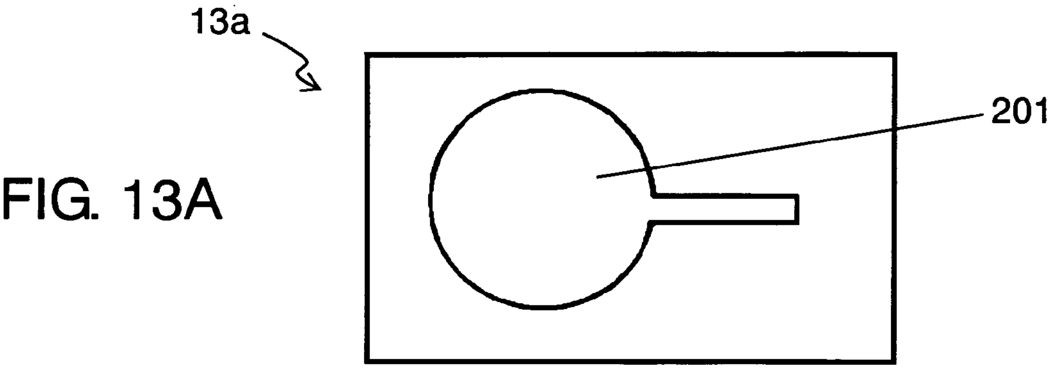
FIGS. 13A, 13B, 13C and 13D are exploded plan views of the nucleic acid amplification reaction vessels used in an experiment in accordance with exemplary embodiment 2.

FIG. 13A shows conventional vessel 13*a* having circular cavity 201 and no columnar structure.

Example 1

Figure 13B:
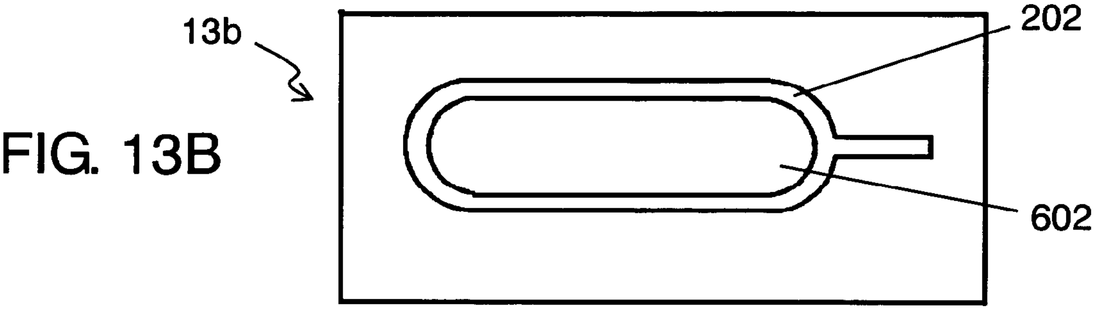

FIG. 13B shows vessel 13*b* having elliptic columnar structure 602 in cavity 202.

Example 2

Figure 13C:
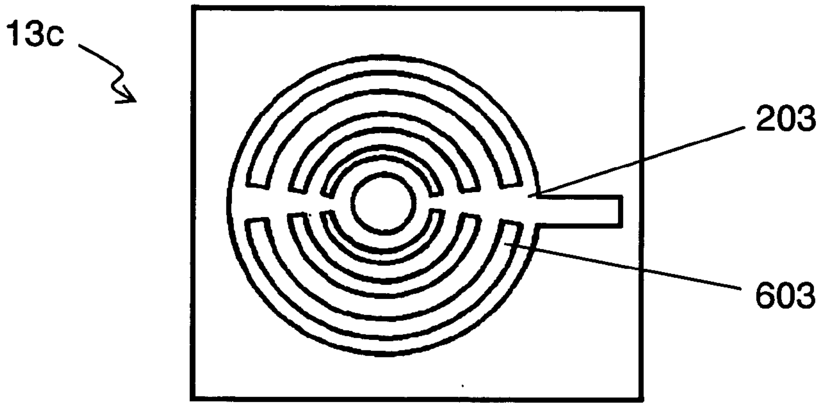

FIG. 13C shows vessel 13*c* having a plurality of bent-shaped columnar structures 603 in cavity 203.

Example 3

Figure 13D:
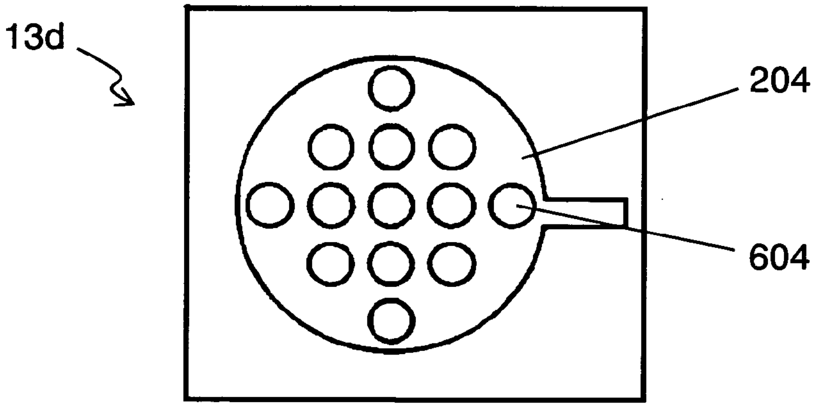

FIG. 13D shows vessel 13*d* having a plurality of circular columnar structures 604 in cavity 204.

This comparative experiment employs LightCycler manufactured by Roche as the thermal cycler device for polymerase chain reaction.

As a nucleic acid amplification reaction using the nucleic acid amplification reaction vessel of the present invention, the polymerase chain reaction is employed. A protocol of performing the polymerase chain reaction is general, so that detailed description is omitted. Material used for performing the polymerase chain reaction is described here.

Firstly, as a template, λ DNA (manufactured by Takara shuzo) (base sequence of λ DNA is shown in GenBank Database Accession No. V00636, J02459, M17233, X00906) is used. As a primer, Control Primer 1 (5'-GATGAGTTCGTGTCCGTACAACTGG-3') and Primer 3 (5'-GAATCACGGTATCCGGCTGCGCTGA-3') (for 300 bp amplification) of TaKaRa Polymerase Chain Reaction Amplification Kit (manufactured by Takara Shuzo) are used.

A sample for polymerase chain reaction containing nucleic acid to be amplified is adjusted (total 50 μl) by mixing 0.5 μl of 2.5 U/μl TaKaRa Z-Taq, 5 μl of 10×Z-Taq Buffer, 4 μl of 2.5 mM each dNTP Mixture, 2.25 μl of 20 pmol/μl Primer 1, 2.25 μl of 20 pmol/μl Primer 3, and 2 μl of 0.25 μg/μl bovine serum albumin in a polypropylene-made tube, then adding 5 μl of 10 ng/μl λ DNA, adding distilled water 29 μl, and slowly mixing them by pipetting.

Next, the adjusted sample is injected into nucleic acid amplification reaction vessels 13*a*, 13*b*, 13*c* and 13*d* of a comparative example and examples 1, 2 and 3. The sample is filled in each nucleic acid amplification reaction vessel by sealing injection hole 4 with heat resistant tape. The nucleic acid amplification reaction vessel filled with the sample is installed in Roche-manufactured LightCycler, and 30 cycles of treatments are repeated under reaction conditions of initial modification reaction 98° C./1 second, modification reaction 98° C./1 second, and annealing and elongating reaction 66° C./4 seconds. Total reaction time is 522 seconds.

After the temperature increasing and decreasing cycles are performed, each nucleic acid amplification reaction vessel is inserted into a centrifugal tube, and centrifugal separation is performed for one minute at rotation speed of 10 k-rpm to recover the sample for polymerase chain reaction from the nucleic acid amplification reaction vessel.

The recovered sample is analyzed with Agilent 2100 Bioanalyser manufactured by Agilent Technology, and 300 bp nucleic acid to be amplified is quantitatively determined.

Figure 14:
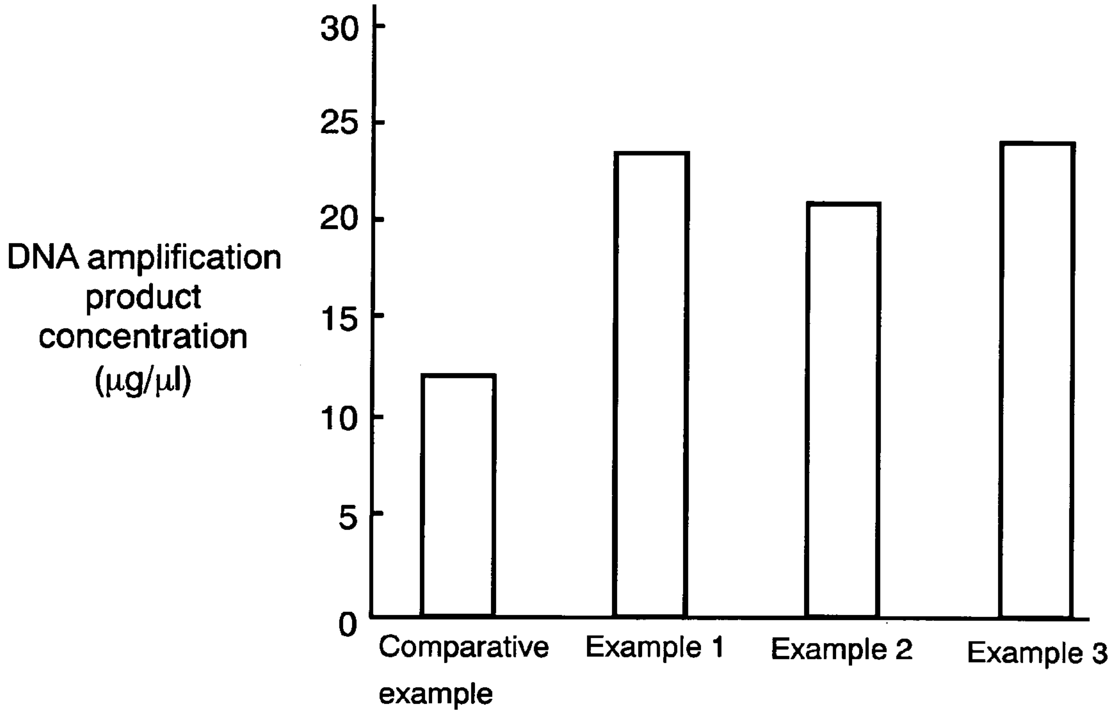
FIG. 14 is a characteristic comparative diagram of polymerase chain reactions using the nucleic acid amplification reaction vessels in accordance with exemplary embodiment 2.

The evaluation result of the nucleic acid amplification reaction is shown in FIG. 14.

According to the result shown in FIG. 14, apparently, any of examples 1, 2 and 3 has more amplification products of the target nucleic acid than that in the comparative example. In the cases where nucleic acid amplification reaction vessels 13*b*, 13*c* and 13*d* of embodiment 2 having a columnar structure in the cavity are used, satisfactory nucleic acid amplification reaction can be performed more efficiently than that in the case where nucleic acid amplification reaction vessel 13*a* of the comparative example having no columnar structure is used.

The nucleic acid amplification reaction vessels of the present invention allow fast temperature increase and decrease of sample liquid and are useful as vessels for amplifying nucleic acid such as polymerase chain reaction vessels.

What is claimed is:

1. A reaction vessel used for amplifying a nucleic acid comprising:

a substrate having a cavity being capable of storing a sample, a cover plate having a sample-injection inlet communicating with the cavity, covers the cavity, and is disposed on the substrate, wherein a plurality of arcuate shape columnar structures are disposed in the cavity, and, a round shape is formed by a pair of the arcuate shape columnar structures in the top view.

2. A reaction vessel according to claim 1, wherein the columnar structure is bonded with one of the cover plate and the substrate by a direct bonding method.

3. A reaction vessel according to claim 1, wherein material of the substrate is silicon and material of the cover plate is glass.

4. An apparatus used for amplifying a nucleic acid comprising:

a reaction vessel of claim 1, and a thermal cycler in which the reaction vessel is located.

5. A manufacturing method of a reaction vessel used for amplifying nucleic acid comprising:

processing a substrate having a cavity being capable of a sample;

forming a cover plate having a sample-injection inlet;

adhering the substrate to the cover plate so that the sample-injection inlet is communicating with the cavity and covers the cavity; and bonding the adhered cover plate and substrate, wherein a plurality of arcuate shape columnar structures are formed when processing the substrate or forming the cover plate so that, after bonding the adhered cover plate and the substrate, the columnar structure is situated in said cavity, and a round shape is formed by a pair of the arcuate shape columnar structures in the top view.

6. A reaction vessel used for amplifying a nucleic acid comprising:

a substrate having a cavity being capable of storing a sample, said cavity having a depth of about 150 to 400 micrometers;

a cover plate having a sample-injection inlet communicating with the cavity, covers the cavity, and is disposed on the substrate, and a columnar structure disposed in the cavity, wherein said columnar structure has a height which is less than a width of said columnar structure;

and the columnar structure has a curved non-circular shape or a bent shape in a top view.

7. A reaction vessel according to claim 6, wherein only one columnar structure is disposed in the cavity.

8. A reaction vessel according to claim 6, wherein the columnar structure is bonded with one of the cover plate and the substrate by a direct bonding method.

9. An apparatus used for amplifying a nucleic acid comprising:

a reaction on vessel of claim 6, and a thermal cycler in which the reaction vessel is located.

10. A reaction vessel according to claim 6, wherein material of the substrate is silicon and material of the cover plate is glass.

* * * * *